United States Patent [19]

Takimoto et al.

[11] 4,416,158
[45] Nov. 22, 1983

[54] PUNCHING-SHEARING METHOD FOR INSPECTING QUALITY OF BUTT WELDED JOINT

[75] Inventors: Tadashi Takimoto, Fuchu; Hirotsugu Oishibashi, Musashino; Katsuyoshi Ueyama, Musashino; Muneyuki Ohara, Musashino; Mitsuo Nakamura, Higashikurume; Takayoshi Amano, Fussa, all of Japan

[73] Assignees: Japanese National Railways; Hakusan Seissaku-sho Co., Ltd., both of Tokyo, Japan

[21] Appl. No.: 345,531

[22] Filed: Feb. 3, 1982

[30] Foreign Application Priority Data

Jun. 18, 1981 [JP] Japan .................................. 56-94327

[51] Int. Cl.³ .............................................. G01N 3/24
[52] U.S. Cl. .................................................. 73/842
[58] Field of Search ............. 73/841, 842, 845, 150 A

[56] References Cited

FOREIGN PATENT DOCUMENTS 1227736 11/1970 U.S.S.R. ................................. 73/841

Primary Examiner—Jerry W. Myracle
Attorney, Agent, or Firm—Wenderoth, Lind & Ponack

[57] ABSTRACT

A punching-shearing method for inspecting the quality of a butt welded joint comprises pressure butt welding steel members under heat to form an annular bulge around the joint portion of the steel members, punching-shearing the bulge under red heat immediately after the pressure butt welding process from one side of the bulge in parallel with the axes of the steel members by use of a shearing die having higher and lower shearing edge portions so that the higher shearing edge portions penetrate the bulge prior to the lower shearing edge portions, so as to cause the base of the bulge to remain around the joint portion in a slightly higher position than the peripheral surfaces of the steel members, and determining the quality of the joint portion from the peripheral surface of the base of the bulge remaining on the joint portion.

2 Claims, 23 Drawing Figures

PUNCHING-SHEARING METHOD FOR INSPECTING QUALITY OF BUTT WELDED JOINT

BACKGROUND OF THE INVENTION

The present invention relates to a method for punching-shearing a bulge formed during a process for pressure butt welding of steel members such as reinforcing bars for the purpose of inspecting the quality of the butt welded joint.

Pressure butt welding of steel members is effected, as widely known to the art, by utilization of either gas heating or electric heating. In the case of the gas pressure butt welding of steel members, pressure is exerted on the steel members toward the butted portions thereof with the butted portions heated by burning gas, thereby expanding the metal (steel) of the heated portions outwardly to form a bulge of a sufficient size around the joint portion and obtaining a welded joint exhibiting given strength. In the case of the electric pressure butt welding of steel members, the steel members are clamped by electrodes, and pressure is exerted on the steel members in the same manner as in the gas pressure butt welding with the heating of the butted portions facilitated by electric resistance due to the flow of electric current, thereby forming a bulge around the joint portion.

Since it is a well-established concept in this field that the strength of the welded joint is enhanced by increasing the cross sectional area of the joint portion, the welded joint is put to practical use in the state wherein the bulge formed during the pressure butt welding process still remains around the joint portion.

To inspect the quality of the butt welded joint, there have heretofore been adopted a fracture testing method on the basis of sampling inspection because of impossibility of determining whether or not the welding is completely effected from the appearance of the surface of the bulge. However, this fracture testing method lacks in reliability when it is desired to inspect the precise state of welding. For this reason, there have also been adopted an ultrasonic flaw detecting method without fracturing any portion in the vicinity of the joint portion. Although this detecting method is advantageous for detecting considerable defects in the welded joint such as existence of unwelded portions in the joint portion due to partial oxidization, presence of surface cracks resulting from superfusion, etc., it entails impossibility of detecting a frequently experienced defect in the welded joint when fractured, which defect is the formation of brittle flat fracture because of the presence of oxides, sulfides, etc. of various sizes in the vicinity of the joint portion in a dispersed state, and has difficulty in detecting the entire surface of the joint portion.

SUMMARY OF THE INVENTION

An object of the present invention is to provide a punching-shearing method capable of determining whether or not the base metals (steel members) are completely pressure welded through observation with the naked eye and of sufficiently guaranteeing the strength of the welded joint even though the joint portion has substantially the same cross sectional area as that of the base metals.

The aforementioned determination and guarantee can be obtained by positively punching-shearing under red heat a bulge to be formed during a process for pressure butt welding of the base metals without worrying about reliability in strength of the welded joint.

To accomplish the object described above according to the present invention, there is provided a punching-shearing method for inspecting the quality of butt welded joint, which comprises subjecting steel members to pressure butt welding process under heat to form an annular bulge around the joint portion of the steel members, subjecting the annular bulge to punching-shearing process under red heat immediately after the pressure butt welding process from one side of the annular bulge in parallel with the axis of the welded joint by use of a shearing die having higher and lower shearing edge portions so that the higher shearing edge portions penetrate the annular bulge prior to the lower shearing edge portions, so as to cause the base of the bulge to remain around the joint portion in a slightly higher position than the peripheral surfaces of the steel members, and determining the quality of the butt welded joint from the peripheral surface of the base of the bulge remaining around the joint portion.

This object and the other objects and characteristic features of the present invention will become apparent from the further disclosure to be made hereinafter in detail with reference to the accompanying drawings.

BRIEF DESCRIPTION OF THE DRAWING

FIG. 12 illustrates another embodiment of the shearing die according to the present invention, in which

DETAILED DESCRIPTION OF THE PREFERRED EMBODIMENT

Figure 1:
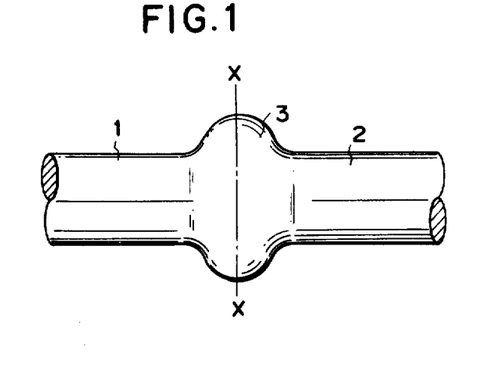
FIG. 1 is a side view illustrating a joint portion of steel members obtained by gas pressure butt welding method.

FIG. 1 illustrates a joint portion obtained by pressure butt welding of steel members 1 and 2. Denoted by 3 is a bulge of the metal formed by the welding.

Figure 2:
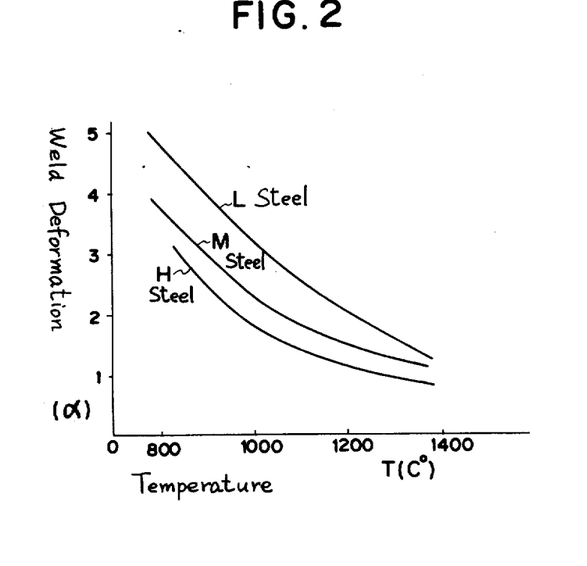
FIG. 2 is a graph showing boundary curves between formation and disappearance of flat fracture in various kinds of steel members.

Steels such as reinforcing rods are classified into high-steel (H steel), medium-steel (M steel) and low-steel (L steel) depending upon the amount of the carbon contents. Generally, in the gas pressure butt welding of H steel members having a high carbon content, a good quality butt welded joint is obtained even at relatively low heating temperatures and at relatively low enlargement degrees of the pressure welding area. This can be confirmed by the fracture test for the joint portion. FIG. 2 shows boundary curves between formation and disappearance of flat fracture in H steel, M steel and L steel respectively, and the lateral axis of the diagram is graduated for heating temperatures T (°C.) and the longitudinal axis thereof for enlargement degrees α of the pressure welding area. In order to obtain a good quality butt welded joint having the joint portion exhibiting a surface of crystalline structure, which will be confirmed by the fracture test, it is necessary to form a bulge 3 so as to make the enlargement degrees α higher than those on the respective α-T curves in FIG. 2.

The term "flat fracture" used throughout the description means a flat, brittle surface containing a plurality of impurities such as oxides, sulfides, etc. and confirmed when the joint portion has been subjected to fracture test. The presence of the flat fracture implies incompletion of the pressure welding. In other words, if there is no such flat fracture in the joint portion, it can be said that the pressure welding has been completely effected.

The present invention relates to a punching-shearing method for determining the quality of the butt welded joint by pressure butt welding steel members 1 and 2 to form a bulge around the joint portion, punching-shearing under red heat immediately after the welding process the bulge 3 at a position which is close to the peripheral surfaces of the steel members as much as possible but is not in alignment with the surfaces while a tear force is given to the joint portion from a single direction, and inspecting the state of the peripheral surface of the base of the bulge 3 remaining around the joint portion immediately after the punching-shearing process and, particularly, precisely grasping the presence of flat fracture and/or cracking in accordance with the state of the entire peripheral surface of the base of the bulge 3 recognized through observation with the naked eye.

The present invention will be described in more detail. As described previously, the bulge 3 is formed around the joint portion of the steel members 1 and 2 by the molten metal expanded by the pressure butt welding by utilization of either gas heating or electrical heating. The bulge 3 is punching-sheared to fulfill the following conditions.

The first condition is to effect the punching-shearing process under red heat immediately after the formation of the bulge 3.

Figure 3:
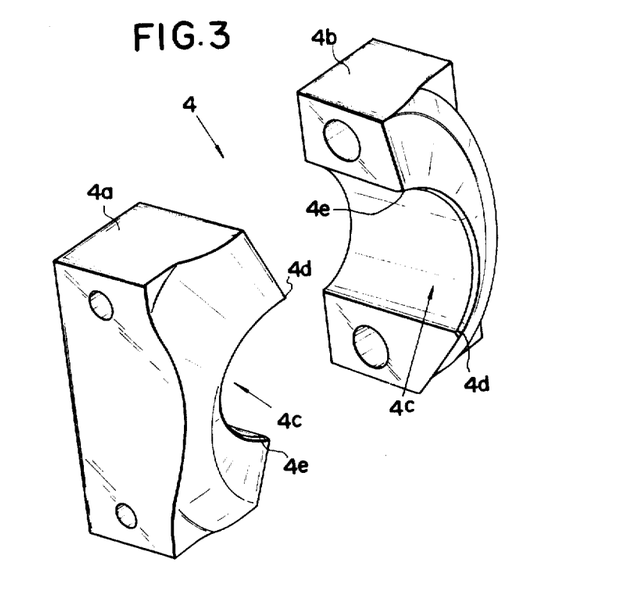
FIG. 3 is a perspective view illustrating a shearing die used in the present invention.
Figure 4A:
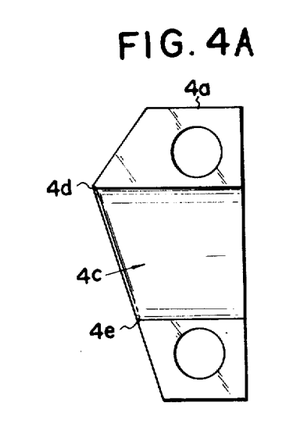
FIG. 4(A) is an inner side view illustrating a divided edge member of the shearing die in FIG. 3.
Figure 4B:
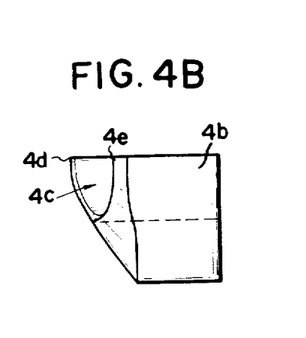
FIG. 4(B) is a top plan view illustrating the divided edge member in FIG. 4(A).
Figure 5:
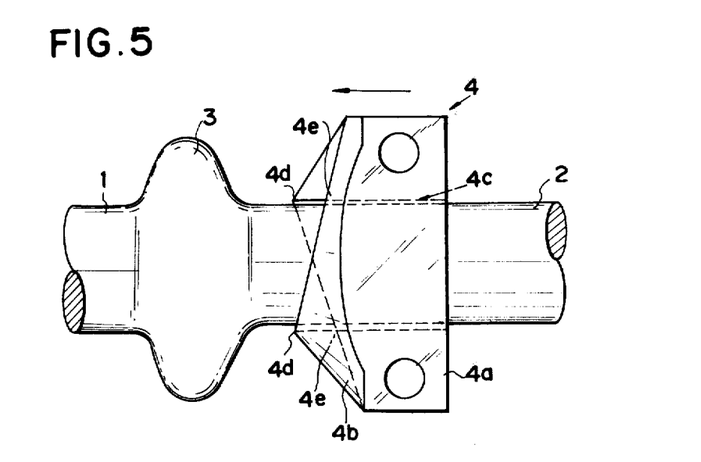
FIG. 5 is a side view showing the application of the shearing die in FIG. 3 to a butt welded joint.
Figure 6A:
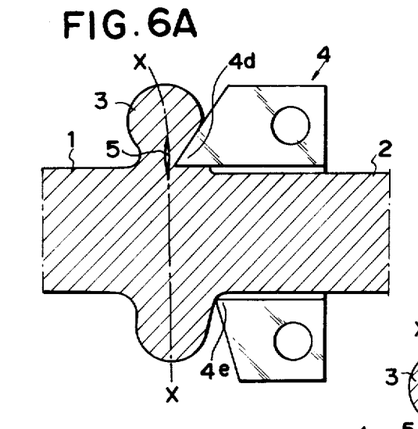
FIGS. 6(A), 6(B), 6(C) and 6(D) are explanatory views illustrating one embodiment of the punching-shearing method according to the present invention.
Figure 6B:
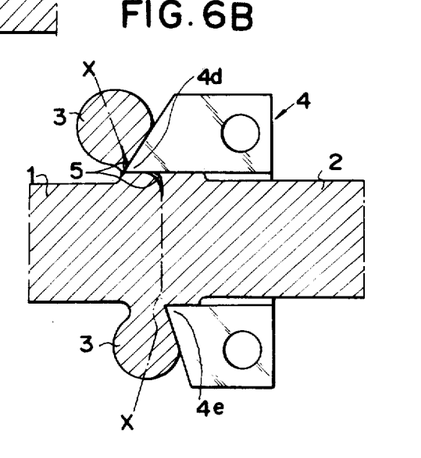
Figure 6C:
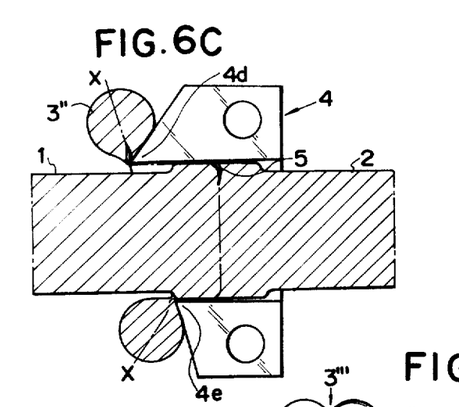
Figure 6D:
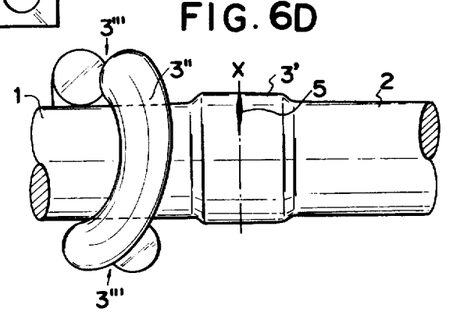
Figure 12A:
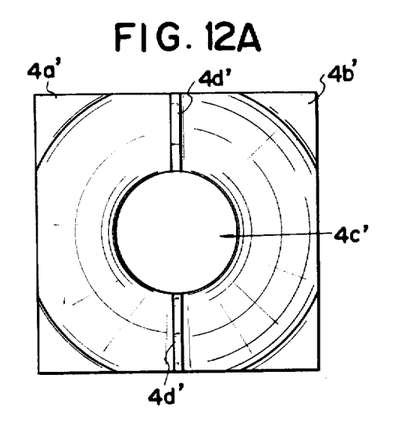
FIG. 12(A) is a front view thereof, FIG. 12(B) a side view thereof and FIG. 12(C) a top plan view thereof.
Figure 12B:
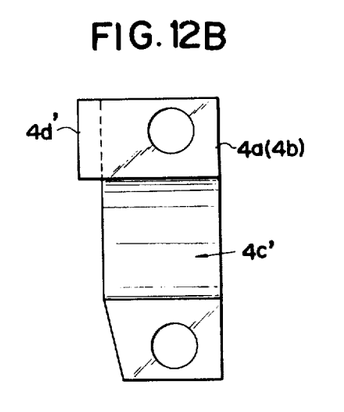
Figure 12C:
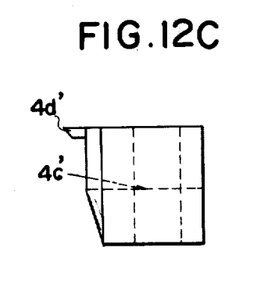

The second condition is that the shearing edges of a shearing die penetrate the bulge 3 from one side thereof in parallel with the axes of the steel members 1 and 2 to effect the punching-shearing process. FIGS. 3 through 5 show one embodiment of the shearing die 4. The shearing die comprises a pair of divided edge members 4a and 4b. The divided edge members 4a and 4b are matched with each other to form an insertion hole 4c for a reinforcing rod. The edge of the insertion hole 4c functions as the shearing edge and surrounds the periphery of the reinforcing rod. The shearing edge has higher edge portions and lower edge portions. The shearing die 4 is divided into two edge members 4a and 4b along the diameter of the insertion hole 4c. The shearing edges of the divided edge members constitute respectively semicircles of the insertion hole 4c. Each of the semicircles has a higher edge portion 4d at one end thereof and a lower edge portion 4e at the other end thereof. The divided edge members 4a and 4b are matched with each other so that the higher edge portions 4d of the divided edge members 4a and 4b are disposed symmetrically relative to the center of the insertion hole 4c. The lower edge portions 4e of the two divided edge members are also symmetrical with respect to the center of the insertion hole 4c and increase their respective heights gradually toward the higher edge portions 4d. FIGS. 12(A), 12(B) and 12(C) illustrate another embodiment of the shearing die of the present invention. This shearing die 4' comprises two divided edge members 4a' and 4b' each having a protruding blade-shaped higher edge portion 4d'. The protruding blade-shaped edge portions 4d' of the divided edge members 4a' and 4b' are disposed in the same manner as the aforementioned higher edge portions 4.

The third condition is to effect the punching-shearing process so that the aforementioned higher edge portions 4d of the shearing die 4 penetrate the bulge 3 prior to the lower edge portions 4e.

The fourth condition is that the bulge 3 is punching-sheared to allow the base 3' of the bulge 3 to slightly remain around the surfaces of the steel members 1 and 2.

It is determined whether or not the pressure welding has been completely effected from the surface of the base 3' of the bulge 3 which has remained around the surfaces of the steel members 1 and 2 in consequence of carrying out the punching-shearing process to fulfill the aforementioned four conditions.

The higher edge portions 4d are caused to penetrate the bulge prior to the lower edge portions 4e. The portion of the bulge penetrated by the higher edge portions is punching-sheared in the axial direction of the steel members prior to the portion of the bulge penetrated by the lower edge portions, thereby punching-shearing the bulge in the form of an annular ring 3" and at the same time further shearing the annular ring at the positions punching-sheared by the higher edge portions at cross section from the inner circumference to the outer circumference of the annular ring. The portions of the ring thus sheared are either cut off or easy to cut off and, therefore, the ring can easily be removed from the welded steel members. Denoted by 3'" is the portions of the ring 3" cut off.

Figure 7A:
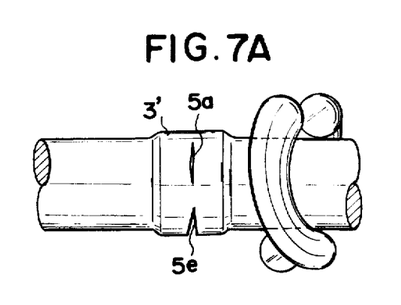
FIGS. 7(A), 7(B) and 7(C) are diagrams illustrating examples of the joint portions of the reinforcing rods obtained by the method of the present invention.
Figure 7B:
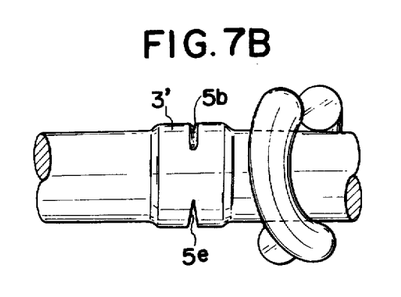
Figures 7C, 7F:
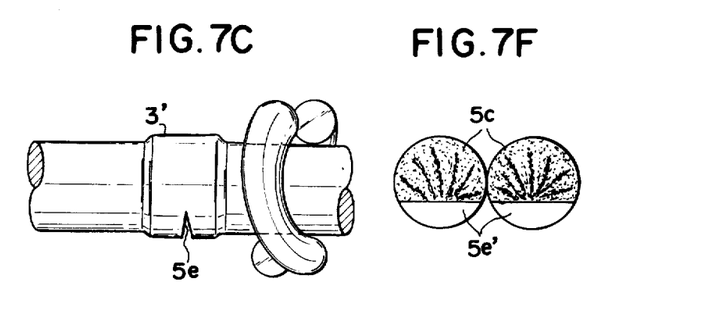
FIGS. 7(D), 7(E) and 7(F) are diagrams showing the cross-sectional states of the joint portions corresponding to those illustrated in FIGS. 7(A), 7(B) and 7(C).
Figure 7D:
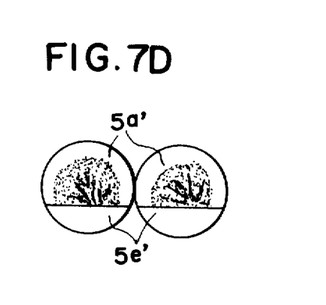
Figure 7E:
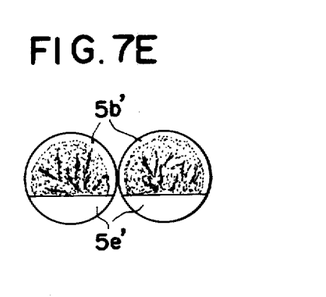
Figure 8:
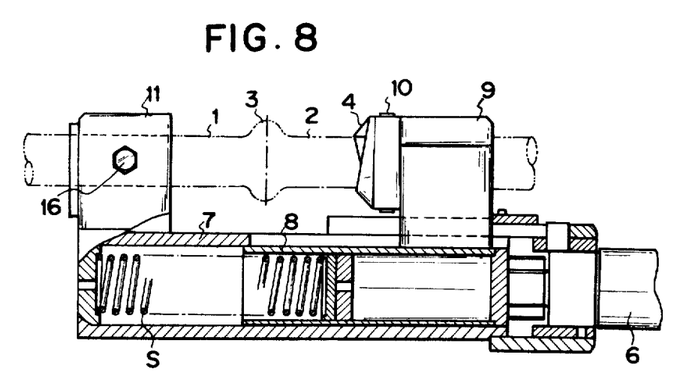
FIG. 8 is a partially cutaway side view illustrating a combination pressure welding and punching-shearing apparatus to be used for carrying out the method of the present invention.
Figure 9:
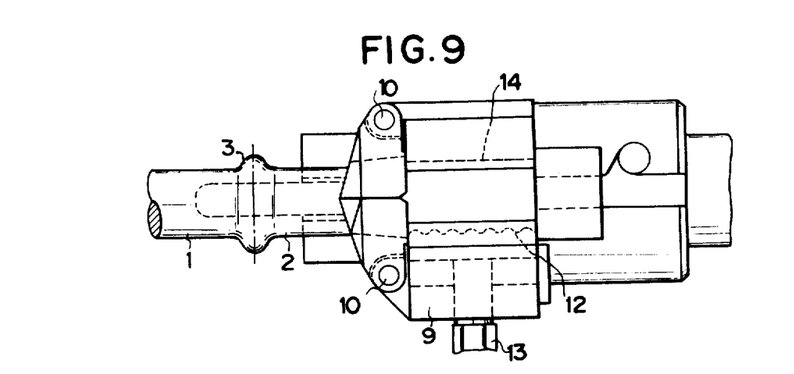
FIG. 9 is a top plan view of the apparatus of FIG. 8.
Figure 10:
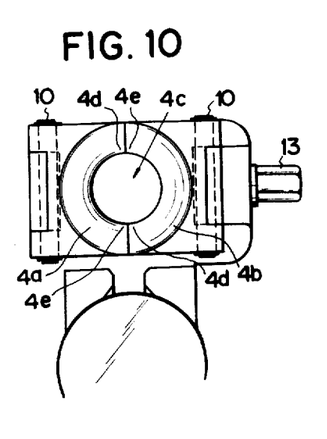
FIG. 10 is a front view illustrating the shearing die of FIG. 3 put to practical use.
Figure 11:
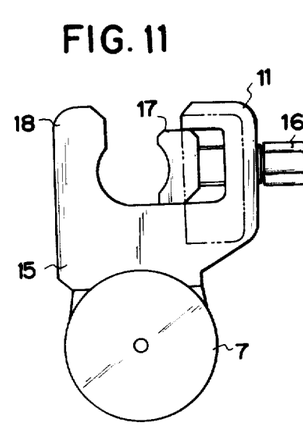
FIG. 11 is a front view illustrating a stationary chuck used in the apparatus of FIG. 8.

FIGS. 7(A) through 7(C) show the states of the peripheral surfaces of the bases of the bulges punching-sheared from the steel members in accordance with the method of the present invention, and FIGS. 7(D) through 7(F) show the states of the interiors of the joint portions of the steel members of FIGS. 7(A) through 7(C), which have been fractured by cutting in advance notches 5e. In these Figures, reference numeral 5e' denotes the surfaces in which the notches 5e are cut.

The higher and lower edge portions of the shearing die 4 penetrate the bulge 3 from the side of one of the steel members along the circumference of the steel members and, in proportion as the penetration proceeds, the joint portion of the steel members is plastically deformed. If the pressure welding is not completely carried out, therefore, cracks are formed in the joint portion as illustrated in FIG. 6.

It has confirmed from a number of experiments that when the joint portion is considerably inferior, the trace formed around the peripheral surface of the base 3' of the bulge 3 is recognized in the form of a clearly cut groove 5a as illustrated in FIG. 7(A), that when such a cut groove 5a is formed, the cut groove extends to the interior of the joint portion and an opened crack 5a' is produced therein as illustrated in FIG. 7(D), that when the joint portion is inferior due to the formation of flat fracture of a relatively low degree, the trace is recognized in the form of a line 5b as illustrated in FIG. 7(B), that when such a line 5b is formed, an unopened crack 5b' is produced in the interior of the joint portion as illustrated in FIG. 7(E), and that when neither a trace nor any annular pattern is formed as illustrated in FIG. 7(C), the joint portion, when fractured, has a surface 5c of crystalline structure as illustrated in FIG. 7(F).

FIGS. 8 through 11 illustrate a punching-shearing apparatus to be used in carrying out the method of the present invention. This apparatus is connected to a hydraulic cylinder 6 and comprises, as illustrated, a cylindrical body 7, a slide member 8 resiliently held by a spring S and inserted into the cylindrical body, a holder 9 rising from the slide member, a shearing die divided into two edge members which are rotatably openably fixed to the holder by means of shafts 10, and a stationary chuck 11 rising from the cylindrical body 7 so as to be opposed to the holder 9.

The holder is provided with a movable chuck mechanism so as to be used both in the gas pressure welding process for the steel members and in the punching-shearing process. In these Figures, reference numeral 12 stands for a movable clamping metal fitting provided in the holder 9, and 14 stands for a stationary clamping metal fitting which is formed by the inner wall of the holder 9 opposed to the movable clamping metal fitting 12. One of the steel members 2 is clamped between the movable and stationary clamping metal fittings 12 and 14 by moving the movable clamping metal fitting 12 with a feed bolt 13. Similarly, the stationary chuck 11 is so constructed that it is provided with a movable clamping metal fitting 17 movably attached to a chuck holder 15 with a feed bolt 16 and also provided with a stationary clamping metal fitting 18 formed by the wall of the chuck holder 15 opposed to the movable clamping metal fitting 17 and that the other steel member 1 is clamped between the two metal fittings 17 and 18.

According to the apparatus of the construction described above, the two steel members 1 and 2 are butted against each other by driving the hydraulic cylinder 6, with one of the two steel members 2 clamped between the clamping metal fittings 12 and 14 of the holder 9 for the shearing die 4 and with the other steel member 1 clamped between the clamping metal fittings 17 and 18 of the stationary chuck 11, thereby effecting pressure welding under heat to form a bulge 3. Upon completion of the pressure welding, the clamping force by means of the clamping metal fittings 12 and 14 is released, the divided edge members are then closed toward each other so as to allow the shearing edges to be close to the periphery of the steel member 2 as much as possible, and subsequently the hydraulic cylinder is driven again, with the result that the bulge 3 can immediately be punching-sheared. Thus, it is possible to obtain a desirable surface punching-sheared without missing a chance of the punching-shearing treatment under red heat and to obtain the pressure welding joint surface necessary for the determination of the quality thereof.

As decribed above, according to the present invention, since it is possible to precisely determine the quality of the interior of the joint portion from the peripheral surface of the base of the bulge remaining around the joint portion in consequence of the punching-shearing treatment, there can be obtained welded joints having extremely high reliability in strength.

Further, since the method of the present invention can be effected by merely having the conventional gas pressure welding apparatus provided with a shearing die and since it can be determined whether or not the pressure welding is completely effected through observation with the naked eye without use of any inspecting instrument, it is possible not only to avoid unreliability in strength entailed by the conventional methods but also to obtain welded joints having reliable strength.

What is claimed is:

1. A punching-shearing method for inspecting the quality of a butt welded joint, which comprises:
   subjecting steel members to a pressure butt welding process under heat to form an annular bulge around a joint portion of the steel members,
   subjecting the annular bulge to punching-shearing process under red heat immediately after the pressure butt welding process from one side of the annular bulge in parallel with the axes of the steel members by use of a shearing die having higher and lower shearing edge portions so that the higher shearing edge portions penetrate the annular bulge prior to the lower shearing edge portions, so as to cause the base of the bulge to remain around the joint portion in a slightly higher position than the peripheral surface of the steel members, and
   determining the quality of the joint portion of the steel members from the peripheral surface of the base of the bulge remaining on the peripheral surface of the joint portion of the steel members.

2. The method according to claim 1, wherein the annular bulge punching-sheared from the steel members is further sheared at a cross section from the inner circumference to the outer circumference of the annular bulge by use of the shearing die.

* * * * *